United States Patent
Zhang et al.

(10) Patent No.: US 10,265,289 B2
(45) Date of Patent: Apr. 23, 2019

(54) METHOD AND MEDICINES FOR TREATING MELANOMA

(71) Applicant: SICHUAN JIUZHANG BIOLOGICAL SCIENCE AND TECHNOLOGY CO., LTD., Chengdu, Sichuan (CN)

(72) Inventors: Jie Zhang, Sichuan (CN); Xiaoguang Chen, Sichuan (CN); Jun Huang, Sichuan (CN); Wang Huang, Sichuan (CN)

(73) Assignee: SICHU JIUZHANG BOPLOGICAL SCIENCE AND TECHNOLOGY CO., LTD., Chengdu, Sichuan (CN)

( * ) Notice: Subject to any disclaimer, the term of this patent is extended or adjusted under 35 U.S.C. 154(b) by 0 days.

(21) Appl. No.: 15/550,681

(22) PCT Filed: Feb. 2, 2016

(86) PCT No.: PCT/CN2016/073124
§ 371 (c)(1),
(2) Date: Aug. 11, 2017

(87) PCT Pub. No.: WO2016/127847
PCT Pub. Date: Aug. 18, 2016

(65) Prior Publication Data
US 2018/0036273 A1    Feb. 8, 2018

(30) Foreign Application Priority Data

Feb. 13, 2015    (CN) .......................... 2015 1 0079033

(51) Int. Cl.
| | | |
|---|---|---|
| A61K 31/216 | (2006.01) |
| A61P 17/00 | (2006.01) |
| A61P 35/00 | (2006.01) |
| A61K 31/05 | (2006.01) |
| A61K 31/191 | (2006.01) |
| A61K 31/337 | (2006.01) |
| A61K 31/513 | (2006.01) |
| A61K 31/675 | (2006.01) |
| A61K 31/704 | (2006.01) |
| A61K 33/24 | (2006.01) |
| A61K 45/06 | (2006.01) |
| A61K 9/00 | (2006.01) |
| C07C 69/732 | (2006.01) |

(52) U.S. Cl.
CPC .......... *A61K 31/216* (2013.01); *A61K 9/0019* (2013.01); *A61K 9/0053* (2013.01); *A61K 31/05* (2013.01); *A61K 31/191* (2013.01); *A61K 31/337* (2013.01); *A61K 31/513* (2013.01); *A61K 31/675* (2013.01); *A61K 31/704* (2013.01); *A61K 33/24* (2013.01); *A61K 45/06* (2013.01); *A61P 17/00* (2018.01); *A61P 35/00* (2018.01); *C07C 69/732* (2013.01); *A61K 2300/00* (2013.01)

(58) Field of Classification Search
CPC .. A61K 31/216; A61K 9/0019; A61K 9/0053; A61K 31/05; A61K 31/191; A61K 31/337; A61K 31/513; A61K 31/675; A61K 31/704; A61K 33/24; A61K 45/06
USPC .......................................................... 514/548
See application file for complete search history.

(56) References Cited

U.S. PATENT DOCUMENTS 7,691,905 B2 *    4/2010  Brooks ................ A61K 31/195
                                                    514/557

FOREIGN PATENT DOCUMENTS

| CN | 100558353 C | 11/2009 |
| CN | 102391119 A | 3/2012 |
| CN | 102579419 B | 2/2014 |

OTHER PUBLICATIONS

Li et al. Molecules 2014, 19, 12940-12948.*
Slomiski et al. Int. J. Cancer. 2009, 124(6), 1470-1477 (Year: 2009).*

* cited by examiner

*Primary Examiner* — Yevgeny Valenrod
(74) *Attorney, Agent, or Firm* — Novick, Kim & Lee, PLLC; Allen Xue

(57) ABSTRACT

The present invention provides an application of chlorogenic acid in preparing medicines for treating melanoma and a pharmaceutical composition comprising chlorogenic acid and used for treating melanoma.

10 Claims, 5 Drawing Sheets

METHOD AND MEDICINES FOR TREATING MELANOMA

TECHNICAL FIELD

The present invention relates to biological medicinal field, especially the treatment field of melanoma, and in particular, relates to uses of chlorogenic acid in the preparation of medicaments for treatment of melanoma, as well as uses of chlorogenic acid in drugs for treatment of melanoma.

BACKGROUND ART

Chlorogenic acid is a phenol isolated from leaves and fruits of dicotylodons (such as *Lonicera japonica* leaves, coffee beans, sunflower), and it is a phenylpropanoid generated from the aerobic respiration process by shikimic acid pathway. Chlorogenic acid is an important constituent widely distributed in various plants, and plants related to daily life, including polly seed, fruits (apple, pear, grape), vegetables (potato), soybean, wheat, cacao bean, coffee bean, fructus hippophae, and traditional Chinese herbals (*Eucommia ulmoides*, Japanese honeysuckle), all contain chlorogenic acid at different degrees.

Chlorogenic acid is a condensed phenolic acid formed by condensation of caffeic acid and quinic acid (1-hydroxyhexahydrogallic acid), and also called caffetannic acid, with a chemical name of 3-O-caffeoylquinic acid, a molecular formula of $C_{16}H_{18}O_9$, and the molecular weight of 345.31. Its semihydrate is obtained as needle crystals, and it becomes an anhydrous compound at 110° C. Chlorogenic acid is easily soluble in hot water, ethanol, and acetone, and slightly soluble in ethyl acetate. At room temperature, it is yellowy or off-white powder.

At present, many pharmacologic actions of chlorogenic acid have already been reported, in which the therapeutic use of chlorogenic acid in cancers is only limited to the report on cervical cancer, lung cancer, liver cancer, and bladder cancer. Wherein, CN200710140602.7 discloses the use of chlorogenic acid in preparation of drugs for treatment of small cell lung cancer; CN201210086313.4 discloses the use of chlorogenic acid in preparation of drugs for treatment of mouse bladder cancer.

So far, there is no report on chlorogenic acid in treating melanoma.

DISCLOSURE OF INVENTION

The inventive object of the present invention is to provide a new use of chlorogenic acid, and particularly, the uses of chlorogenic acid in the preparation of medicaments for treatment of melanoma, as well as uses of chlorogenic acid in drugs for treatment of melanoma. By experiments, the present invention proves that chlorogenic acid can promote the polarization of monocytes to type M1 macrophages, inhibit the polarization of monocytes to type M2 macrophages, suppress transformation of type M1 macrophages to type M2 macrophages, as well as facilitate transformation of type M2 macrophages to type M1 macrophages, and finally achieve the purpose of treating melanoma.

In order to accomplish above purposes, the present invention uses the following technical solution:

Uses of chlorogenic acid in the preparation of medicaments for treatment of melanoma.

Medicaments are prepared by using chlorogenic acid as active components, with addition of pharmaceutically acceptable excipients or auxiliary materials.

In said medicament, a preparation unit contains 1-1000 mg of chlorogenic acid.

Its mechanism of action is that chlorogenic acid realizes its uses in treatment of melanoma by regulating polarization of macrophages.

Chlorogenic acid realizes its uses in treatment of melanoma and controlling metastasis of melanoma by promoting polarization of monocytes to type M1 macrophages.

Chlorogenic acid realizes its uses in treatment of melanoma and controlling metastasis of melanoma by inhibiting polarization of monocytes to type M2 macrophages.

Chlorogenic acid realizes its uses in treatment of melanoma and controlling metastasis of melanoma by inhibiting polarization of type M1 macrophages to type M2 macrophages and promoting transformation of type M2 macrophages to type M1 macrophages.

The uses of chlorogenic acid and chemotherapeutic drugs in preparation of drug combination for treatment of melanoma.

Said chemotherapeutic drugs are selected from the group of cisplatin, 5-fluorouracil, paclitaxel, adriamycin, and cyclophosphamide.

A medicament for treatment of melanoma, and its active component is chlorogenic acid.

The medicament is prepared by using chlorogenic acid as active components, with addition of pharmaceutically acceptable excipients or auxiliary materials Macrophages participate the occurrence and progress of tumors, and different polarization types (M1, M2) of macrophages play different roles in tumorigenesis. M1-type macrophages kill tumor cells by various pathway; while M2-type macrophages take part in the process of tumor occurrence, growth, invasion and metastasis, and are usually shown to facilitate the process of the tumor growth, the tumor angiogenesis, and the metastasis of tumor cells. Tumor local microenvironments encourage the differentiation of tumor-associated macrophages (TAMs) to M2-type macrophages. Investigation shows that TAMs behave as M1-type at initial stage of tumor, but behaves as M2-type at progression stage. Similarly, a large number of researches show that TAMs present in tumor tissues mostly behave as M2 phenotype, and are related to the treatment and prognosis of tumors. Wherein, the signal pathway for polarization of M1-type macrophages is as follows: IFN-γ activates the pathway for signal transducer and activator of transcription (STAT1) by IFNR, directly promotes the up-regulation of expression of genes IL-2, NOS2, and MHC II, and these are the essential conditions for polarization of M1-type macrophages. Currently, discoverable M1 surface markers include IL-6, IL-12, iNOS, TNF-α, MAPKO acceptor, CD80, CD86, TLR-2, TLR-4, FcRIII(CD16), CD32, CD62, IL-1R1, CD127, etc, and in the ordinary study, the commonly used is iNOS, TNF-α, IL-12, etc.

The activation pathway of M2-type macrophages was mainly mediated by STAT6. The signal pathway for polarization of M2-type macrophages is as follows. Firstly, IL-4 binds to IL-4Rα and IL-12Rγ receptors (type I receptor). Or IL-4 and IL-13 bind respectively to its receptors IL-4Rα and IL-13Rα. After dimerization of receptors (type II receptor), Janus kinases Jak1/Jak3 or Jak1/Jak2/Tyk2 is activated. Thus, the main member IRS of insulin receptor substrate family is collected to form complexes. Phosphorylated IRS activates adapter proteases Grb2 and PI3K, to further collect STAT6. and make STAT6 tyrosine phosphorylated. Phosphorylated IRS forms dimmers, and after entering the nucleus, the dimmers trigger the transcription of M2 function associated genes, promoting the polarization of macrophages to M2-type. Surface markers of M2-type macrophages include arginase 1(Arg1), mannose receptor (MRC1, CD206), CD163, FcR2(CD23, CD209), FIZZ1, ST2, SR-A, M60 acceptor CD184, TRAIL, etc. The commonly-used includes Arg1, MRC1FIZZ1, and some chemotactic factors, etc.

By investigation, the applicants discover it has obvious effect that chlorogenic acid can used for preventing and treating melanoma, as well as controlling its metastasis. Experiments show that chlorogenic acid can promote the polarization of monocytes to type M1 macrophages, inhibit the polarization of monocytes to type M2 macrophages, at the same time, suppress transformation of type M1 macrophages to type M2 macrophages, facilitate transformation of type M2 macrophages to type M1 macrophages, and finally achieve the purpose of preventing and treating melanoma, as well as controlling its metastasis.

Based on above findings, using various pharmacy technologies, chlorogenic acid can be solely or together with other drugs having known efficacy prepared as injectable preparations, oral preparations and so on.

Above efficacy of chlorogenic acid is proved by following experiments. It should be understood that examples of the present invention are used to elucidate the present invention and do not limit the present invention. The simple changes to the present invention, made as the spirit of the present invention, all belong to the scope claimed by the present invention.

BRIEF DESCRIPTION OF DRAWINGS

The present invention is illustrated by examples and referring to Figures, in which.

Figure 1:
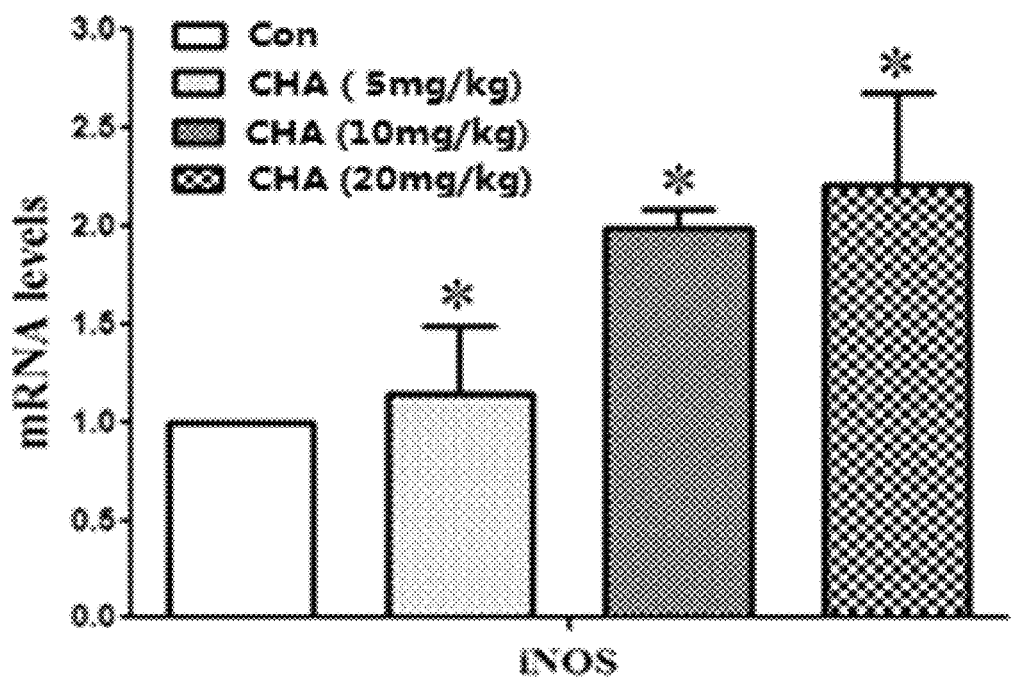
FIG. 1 is the detection result graph of iNOS expression in example 1.

Description of the Preferred Embodiments in the present specification, all disclosed features or all disclosed methods or steps in the process can be combined in any way except for mutually exclusive features and/or steps.

In the present specification, any disclosed feature can be replaced by other equivalent or similar alternative features, unless particular statement. That is, unless particular statement, each feature only is an example of a series of equivalent or similar features.

EXAMPLE 1 CHLOROGENIC ACID PROMOTES POLARIZATION OF MONOCYTES TO M1-TYPE MACROPHAGES (1) Animal Model Establishment Mouse melanoma B16 model chooses male C57BL/6 mice, weighing 18-22 g. At the experiment, the tissue of tumor grown well was taken out, sheared, ground, filtered, and then diluted with sterile normal saline at a ratio of 1:3, to prepare suspension of tumor cells. 0.2 ml tumor cell suspension was inoculated on the axillary back of each mouse. After successful inoculation, animals were divided into groups next day, weighed, and administration of drugs started. The dosage volume of chlorogenic acid injection was 0.2 ml/10 g mouse by intraperitoneal injection, once a day, and the administration continued for 13 days.

Laboratory animals were divided into four groups, including negative control group, three chlorogenic acid groups at a dosage of 5 mg/kg, 10 mg/kg, and 20 mg/kg. Each group has 15 animals. Next day, after withdrawal of chlorogenic acid, animals were sacrificed and weighed, then tumors were peeled and weighed. Tumor control rate (%) was calculated based on tumor weight. Body weight and tumor weight were expressed as mean±standard deviation (x±SD).

(2) Sample Collection

After successful anesthesia of mice, bilateral eyeballs were removed and mice were killed by bleeding. After confirming that mice did not have autonomous heartbeat, mice were handed and placed in 75% alcohol to macerate for 5-10 seconds, then mice were taken out and their four limbs were immobilized on mouse operation table. Mice were placed in supine position, with segmental venter being toward up. 5 ml serum-free DMEM medium preheated at 37° C. was drawn out using 5 ml aseptic syringe, and middle-lower abdominal skin of mice was lifted with a tweezer, then 5 ml pre-suctioned serum-free DMEM medium preheated at 37° C. was injected to abdominal cavity (note: needlepoint being toward up, avoiding intestinal canal and fat). After that, bilateral peritoneal wall was gently kneaded and pressed for about 20-30 seconds, to make the intraperitoneal fluid fully flow. When collecting the peritoneal fluid, a little cut was opened on mouse hypogastric region using a surgical scissor, and skin was teared toward two sides, to thoroughly expose the peritoneum, then it was wiped and cleaned with 75% alcoholic cotton balls for sterilization. Further, about 0.5-1 cin of little cut was opened on mouse peritoneum using ophthalmic scissors, and the peritoneal fluid was drawn back with 5 ml aseptic syringe (Try not to absorb intestinal canal and fat, otherwise, it is easy to cause contamination of fibroblasts), then transferred to 15.0 ml centrifuge tube and centrifugated at 1200 rpm/min for 5 min, to remove the supernatant fluid. The residue was re-suspended in sterile normal saline at 1200ˆ1 and transferred into 1.5 ml centrifuge tube for use.

To sheared tumor tissue, 10 times volume (based on tumor tissue volume) of enzyme working solution (IX, containing IV-type collagenase (1 mg/ml), hyaluronidase (1%), DNA enzyme 1 (0.25%)) was added according to the tissue precipitation volume, and the centrifuge tube was placed on 37t: water bath for about 2 h of digestion till the tumor tissue was thoroughly digested. During enzymatic digestion, centrifuge tubes were shaken every 10-15 minutes. When the fluid in centrifuge tubes became turbid, the piece of tumor tissue had already disintegrated and lost its massive shape. Once being shaken, the mass would become cell clumps or single cell, indicating the tumor tissue piece had already been fully digested. The enzymatic digestion time can be suitably shortened or elongated as the digestion degree of tumor tissue. The fluid was well blended, and the digestive juices of tumor tissue was suctioned, filtered through 7 (Hun stainless steel screen to 15.0 ml new centrifuge tubes, to get rid of undigested larger tissue lump, then centrifuged at 1200 rpm/min for 5 min, to remove the supernatant fluid. Cells were re-suspended in sterile normal saline at 1200^1, and transferred to 1.5 ml centrifuge tubes for use.

Figure 2:
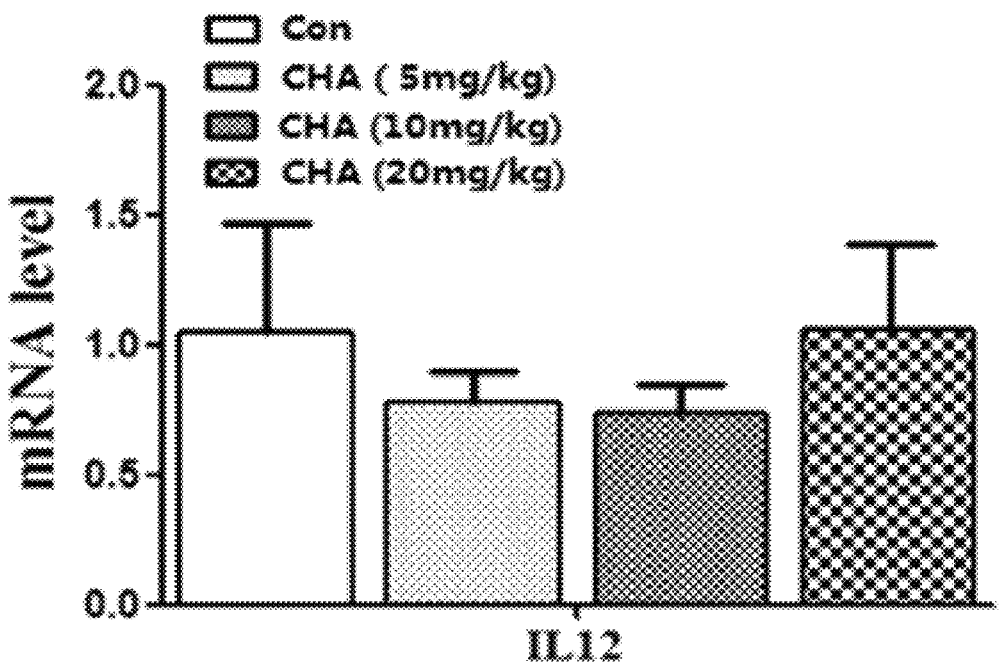
FIG. 2 is the detection result graph of IL-12 expression in example 1.
Figure 3:
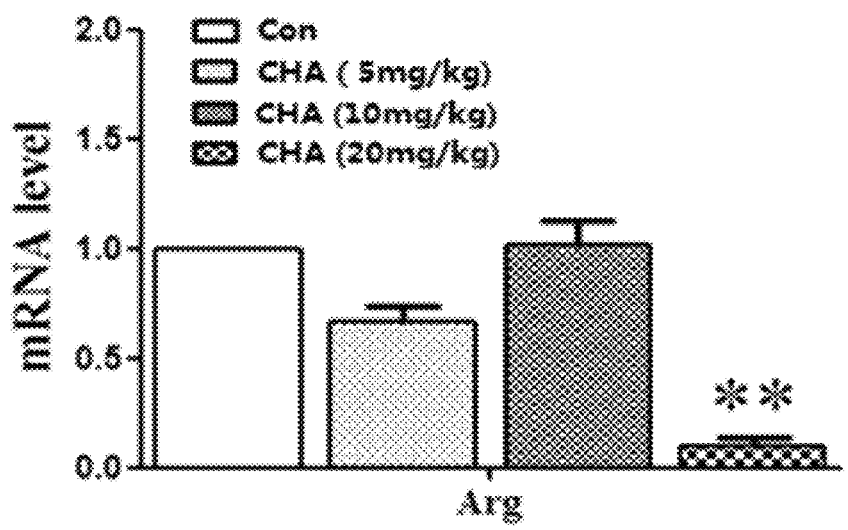
FIG. 3 is the detection result graph of Arg expression in example 1.
Figure 4:
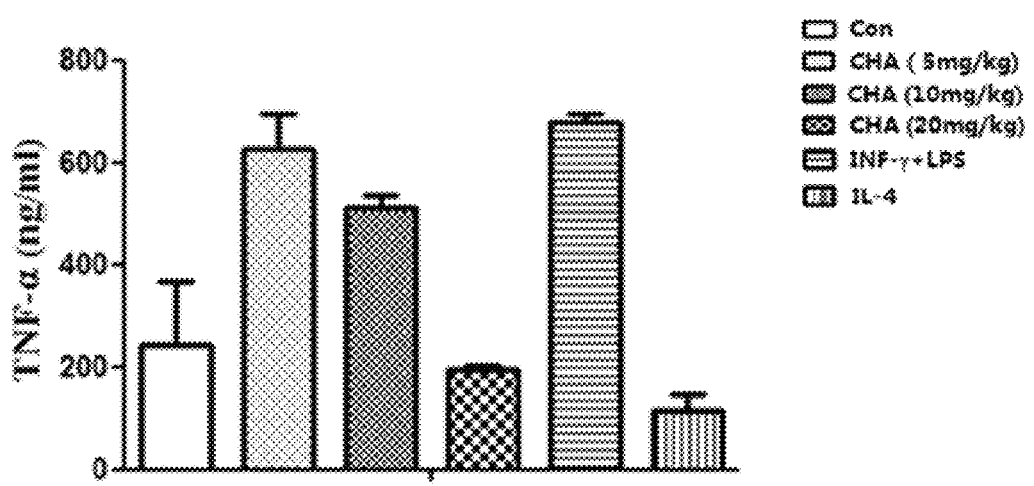
FIG. 4 is the detection result graph of TNF-α expression in example 1.

(3) Cell phenotype was detected by flow cytometer, and the corresponding marker of same sample was determined using real-time fluorescent quantified PCR. Results were shown in FIGS. 1-3, in which FIGS. 1-3 are respectively the detection result graphs of iNOS, IL-12, Arg expression in example 1. FIG. 4 is the detection result graph of TNF-α expression in example 1.

FIGS. 1 and 2 showed that chlorogenic acid can obviously promote the expression of M1-type macrophage markers iNOS and IL-12, and which presents a dose-dependent relationship. At a dosage of 20 mg/kg, the promotive effect was the strongest. FIG. 3 clearly showed that chlorogenic acid can obviously inhibit the expression of M2-type macrophage markers Arg, and which have a dose-dependent relationship. At the dosage of 20 mg/kg, the inhibitory effect was the strongest; FIG. 4 shows that chlorogenic acid can promote the expression of M1-type macrophage marker TNF-α. In animal melanoma models, results suggested that chlorogenic acid can facilitate the polarization of monocytes to M1-type macrophages, thus had an obvious anti-tumor effect.

EXAMPLE 2 CHLOROGENIC ACID MAINTAINS M1-TYPE MACROPHAGES, INHIBITS THE POLARIZATION OF M1-TYPE TO M2-TYPE

Mouse melanoma B16 model chooses male C57BL/6 mice, weighing 18-22 g. At the experiment, the tissue of tumor grown well was taken out, sheared, ground, filtered, and then diluted with sterile normal saline at a ratio of 1:3 to prepare suspension of tumor cells. 0.2 ml tumor cell suspension was inoculated on the axillary back of each mouse. After successful inoculation, animals were divided into groups next day, weighed, and administration of drugs started. The dosage volume of chlorogenic acid injection was 0.2 ml/10 g mouse by intraperitoneal injection, once a day, and the administration continued for 13 days.

Laboratory animals were divided into four groups, including (1) control group (LPS+INFγ), (2) 5 mg/kg drug combination group of LPS and INFγ and chlorogenic acid, (3) 10 mg/kg drug combination group of LPS and INFγ and chlorogenic acid, (4) 20 mg/kg drug combination group of LPS and INFγ and chlorogenic acid. Each group includes 15 animals.

(2) Sample Collection

After successful anesthesia of mice, bilateral eyeballs were removed and mice were killed by bleeding. After confirming that mice did not have autonomous heartbeat, mice were handed and placed in 75% alcohol to macerate for 5-10 seconds, then mice were taken out and their four limbs were immobilized on mouse operation table. Mice were placed in supine position, with segmental venter being toward up. 5 ml serum-free DMEM medium preheated at 37° C. was drawn out using 5 ml aseptic syringe, and middle-lower abdominal skin of mice was lifted with a tweezer, then 5 ml pre-suctioned serum-free DMEM medium preheated at 37° C. was injected to abdominal cavity (note: needlepoint being toward up, avoiding intestinal canal and fat). After that, bilateral peritoneal wall was gently kneaded and pressed for about 20-30 seconds, to make the intraperitoneal fluid fully flow. When collecting the peritoneal fluid, a little cut was opened on mouse hypogastric region using a surgical scissor, and skin was teared toward two sides, to thoroughly expose the peritoneum, then it was wiped and cleaned with 75% alcoholic cotton balls for sterilization. Further, about 0.5-1 cin of little cut was opened on mouse peritoneum using ophthalmic scissors, and the peritoneal fluid was drawn back with 5 ml aseptic syringe (Try not to absorb intestinal canal and fat, otherwise, it is easy to cause contamination of fibroblasts), then transferred to 15.0 ml centrifuge tube and centrifugated at 1200 rpm/min for 5 min, to remove the supernatant fluid. The residue was re-suspended in sterile normal saline at 1200^1 and transferred into 1.5 ml centrifuge tube for use.

To sheared tumor tissue, 10 times volume (based on tumor tissue volume) of enzyme working solution (IX, containing IV-type collagenase (1 mg/ml), hyaluronidase (1%), DNA enzyme 1 (0.25%)) was added according to the tissue precipitation volume, and the centrifuge tube was placed on 37t: water bath for about 2 h of digestion till the tumor tissue was thoroughly digested. During enzymatic digestion, centrifuge tubes were shaken every 10-15 minutes. When the fluid in centrifuge tubes became turbid, the piece of tumor tissue had already disintegrated and lost its massive shape. Once being shaken, the mass would become cell clumps or single cell, indicating the tumor tissue piece had already been fully digested. The enzymatic digestion time can be suitably shortened or elongated as the digestion degree of tumor tissue. The fluid was well blended, and the digestive juices of tumor tissue was suctioned, filtered through 7 (Hun stainless steel screen to 15.0 ml new centrifuge tubes, to get rid of undigested larger tissue lump, then centrifuged at 1200 rpm/min for 5 min, to remove the supernatant fluid. Cells were re-suspended in sterile normal saline at 1200^11, and transferred to 1.5 ml centrifuge tubes for use.

(3) Cell phenotype was detected by flow cytometer, and the corresponding marker of same sample was determined using real-time fluorescent quantified PCR. Results were shown in FIGS. 5-6, in which FIGS. 5 and 6 are respectively the detection result graphs of M1-type macrophage marker iNOS expression and M2-type macrophage marker Arg expression in example 2.

Figure 5:
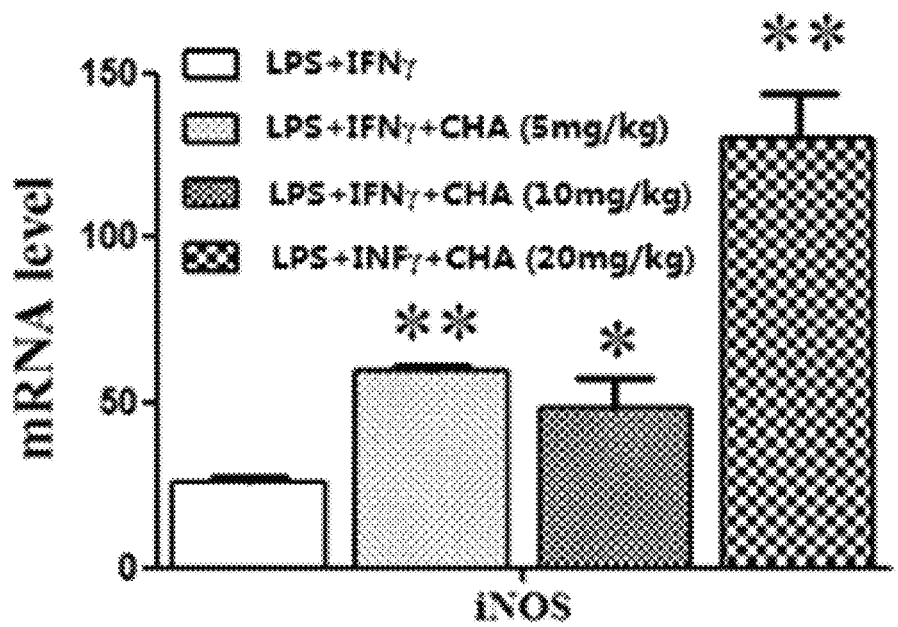
FIG. 5 is the detection result graph of M1-type macrophage marker iNOS expression in example 2.
Figure 6:
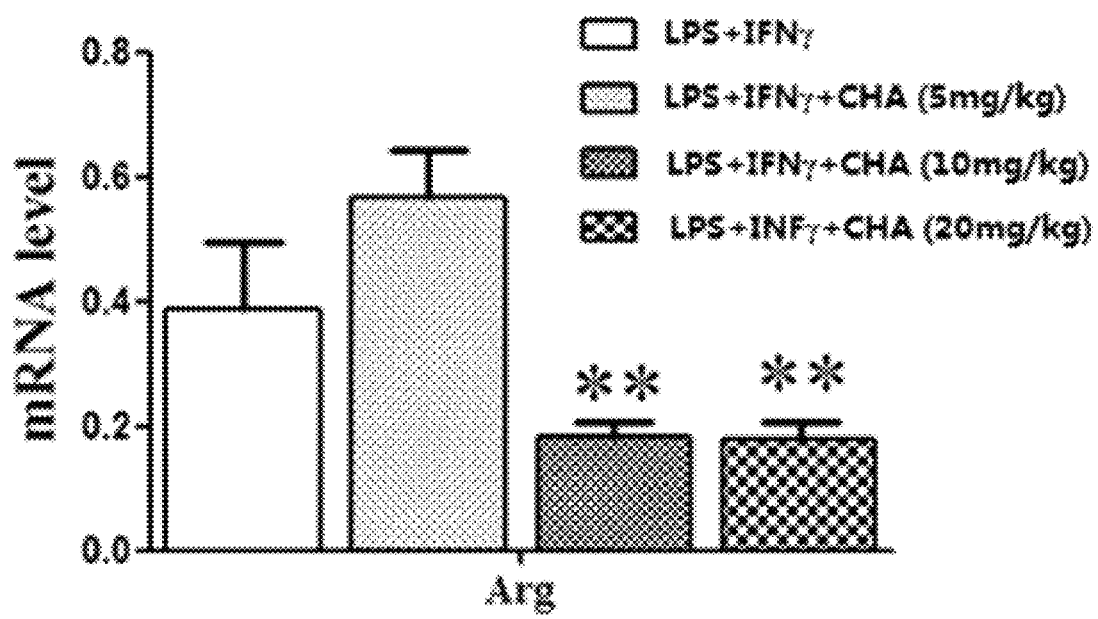
FIG. 6 is the detection result graph of M2-type macrophage marker Arg expression in example 2.

FIG. 5 shows that chlorogenic acid can maintain the high expression state of M1-type macrophage markers, and which presents a dose-dependent relationship. At a dosage of 20 mg/kg, M1-type macrophage is hold at the highest state. FIG. 6 shows that chlorogenic acid can maintain M2-type macrophage markers Arg at relatively lower state, and which represents a dose-dependent relationship. Above results indicated that under the action of chlorogenic acid, M1-type macrophages did not transform to M2-type macrophages. In animal melanoma models, chlorogenic acid can remain the amount of M1-type macrophages, inhibit the transformation of M1-type macrophages to M2-type macrophages, thus play a role in inhibiting growth of melanoma cells and realize anti-tumor effect.

EXAMPLE 3 CHLOROGENIC ACID PROMOTES TRANSFORMATION OF M2-TYPE MACROPHAGES TO M1-TYPE MACROPHAGES (1) Animal Model Establishment Mouse melanoma B16 model chooses male C57BL/6 mice, weighing 18-22 g. At the experiment, the tissue of tumor grown well was taken out, sheared, ground, filtered, and then diluted with sterile normal saline at a ratio of 1:3, to prepare suspension of tumor cells. 0.2 ml Tumor cell suspension was inoculated on the axillary back of each mouse. After inoculation, animals were divided into groups next day, weighed, and administration of drugs started. The dosage volume of chlorogenic acid injection was 0.2 ml/10 g mouse by intraperitoneal injection, once a day, and the administration continued for 13 days.

Laboratory animals were divided into five groups, including (1) negative control group, (2) control group (IL-4), (3) 5 mg/kg drug combination group of IL-4 and chlorogenic acid, (4) 10 mg/kg drug combination group of IL-4 and chlorogenic acid, (5) 20 mg/kg drug combination group of IL-4 and chlorogenic acid. Each group includes 15 animals.

(2) Sample Collection

After successful anesthesia of mice, bilateral eyeballs were removed and mice were killed by bleeding. After confirming that they did not have autonomous heartbeat, mice were handed and placed in 75% alcohol to macerate for 5-10 seconds, then mice were taken out and their four limbs were immobilized on mouse operation table. Mice were placed in supine position, with segmental venter being toward up. 5 ml serum-free DMEM medium preheated at 37° C. was drawn out using 5 ml aseptic syringe, and middle-lower abdominal skin of mice was lifted with a tweezer, then 5 ml medium was injected to abdominal cavity (note: needlepoint being toward up, avoiding intestinal canal and fat). After that, bilateral peritoneal wall was gently kneaded and pressed for about 20-30 seconds, to make the intraperitoneal fluid fully flow. When collecting the peritoneal fluid, a little cut was opened on mouse hypogastric region using a surgical scissor, and skin was teared toward two sides, to thoroughly expose the peritoneum, then it was wiped and cleaned with 75% alcoholic cotton balls for sterilization. Further, about 0.5-1 cin of little cut was opened on mouse peritoneum using ophthalmic scissors, and the peritoneal fluid was drawn back with 5 ml aseptic syringe (Try not to absorb intestinal canal and fat, otherwise, it is easy to cause contamination of fibroblasts), then transferred to 15.0 ml centrifuge tube and centrifugated at 1200 rpm/min for 5 min, to remove the supernatant fluid. The residue was re-suspended in sterile normal saline at 1200^1 and transferred into 1.5 ml centrifuge tube for use. To sheared tumor tissue, 10 times volume (based on tumor tissue volume) of enzyme working solution (IX, containing IV-type collagenase (1 mg/ml), hyaluronidase (1%), DNA enzyme 1 (0.25%)) was added according to the tissue precipitation volume, and the centrifuge tube was placed on 37t: water bath for about 2 h of digestion till the tumor tissue was thoroughly digested. During enzymatic digestion, centrifuge tubes were shaken once every 10-15 minutes. When the fluid in centrifuge tubes became turbid, the piece of tumor tissue had already disintegrated and lost its massive shape. Once being shaken, the mass would become cell clumps or single cell, indicating the tumor tissue piece had already been fully digested. The enzymatic digestion time can be suitably shortened or elongated as the digestion degree of tumor tissue. The fluid was well blended, and the digestive juices of tumor tissue was suctioned, filtered through 7 (Hun stainless steel screen to 15.0 ml new centrifuge tubes, to get rid of undigested larger tissue lump, then centrifuged at 1200 rpm/min for 5 min, to remove the supernatant fluid. Cells were re-suspended in sterile normal saline at 1200^11, and transferred to 1.5 ml centrifuge tubes for use.

(3) Cell phenotype was detected by flow cytometer, and the corresponding marker of same sample was determined using real-time fluorescent quantified PCR. Results were shown in FIGS. 5-9, in which FIGS. 7-8 are respectively the detection result graphs of iNOS expression, IL-10 expression, and Arg expression in example 3.

Figure 7:
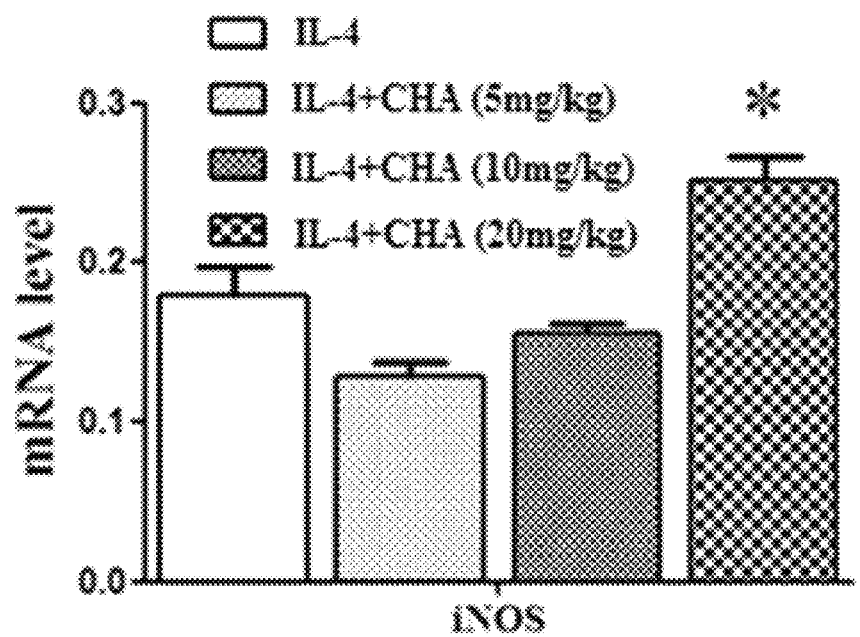
FIG. 7 is the detection result graph of iNOS expression in example 3.
Figure 8:
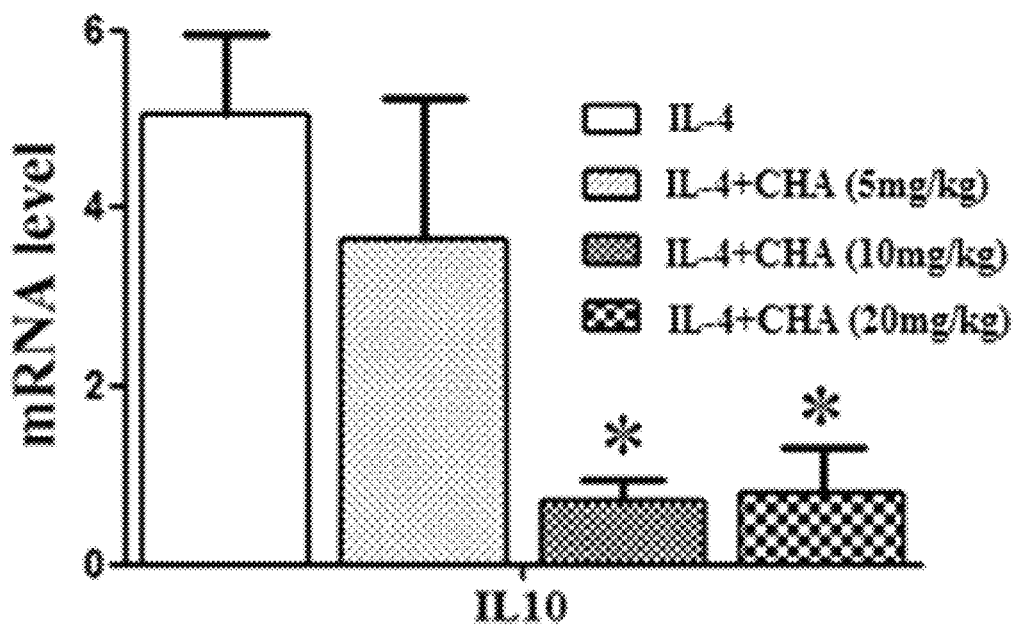
FIG. 8 is the detection result graph of IL10 expression in example 3.
Figure 9:
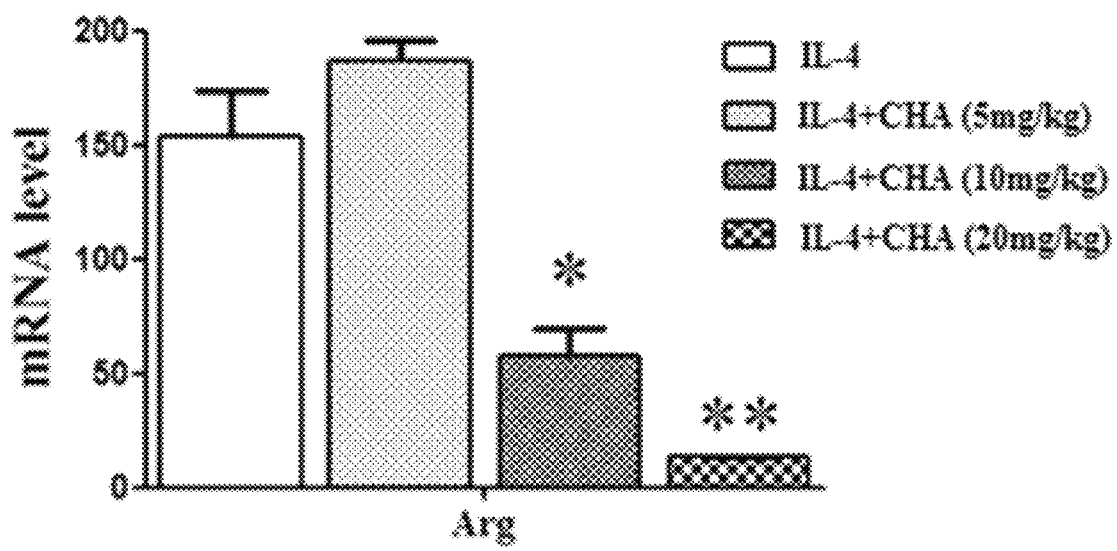
FIG. 9 is the detection result graph of Arg expression in example 3.

FIG. 7 shows that in the same sample, the growth of M1-type macrophage cells presents a positive correlation with the dose of chlorogenic acid; FIG. 8 shows that the growth of M2-type macrophage cells presents a negative correlation with the dose of chlorogenic acid. In animal melanoma models, chlorogenic acid can promote the transformation of M2-type macrophages to M1-type macrophages.

EXAMPLE 4 TUMOR INHIBITORY RATE OF CHLOROGENIC ACID AGAINST ANIMAL MELANOMA MODELS (1) Experimental Methods Mouse melanoma B16 model chooses male C57BL/6 mice, weighing 18-22 g. At the experiment, the tissue of tumor grown well was taken out, sheared, ground, filtered, and then diluted with sterile normal saline at a ratio of 1:3, to prepare suspension of tumor cells. 0.2 ml Tumor cell suspension was inoculated on the axillary back of each mouse. After inoculation, animals were divided into groups next day, weighed, and administration of drugs started. The dosage volume of chlorogenic acid injection was 0.2 ml/10 g mouse by intraperitoneal injection, once a day, and the administration continued for 13 days.

Laboratory animals were divided into five groups, including (1) negative control group, (2) 60 mg/kg cyclophosphamide group, (3) 5 mg/kg chlorogenic acid group, (4) 10 mg/kg chlorogenic acid group, (5) 20 mg/kg chlorogenic acid group. Each group includes 15 animals. Next day after withdrawal of chlorogenic acid, animals were sacrificed and weighed, then tumors were peeled and weighed. Tumor control rate (%) was calculated based on tumor weight. Body weight and tumor weight were expressed as mean±standard deviation (x±SD). Each drug-administration group and the negative control group were compared.

(2) Experimental Results

Administration of chlorogenic acid to tumor-bearing mice by intraperitoneal injection shows obviously inhibitory effect on growth of mouse melanoma B16, and presents certain dose-effect relationship. Tumor inhibitory rate of 20 mg/kg chlorogenic acid is close to that of cyclophosphamide. At dosage used, chlorogenic acid did not have obvious effect on animal body weight, as shown in Table 1.

TABLE 1

Anti-tumor effect of chlorogenic acid against mouse melanoma B16

| Groups | Dosage (mg/kg × time) | Animal No. Initial/End | Body weight (g) $\bar{x} \pm SD$ Initial | Body weight (g) $\bar{x} \pm SD$ End | Tumor weight (g) $\bar{x} \pm SD$ | Tumor inhibitory rate (%) |
|---|---|---|---|---|---|---|
| Negative control group | | 15/15 | 21.00 ± 0.55 | 21.79 ± 1.25 | 3.27 ± 0.89 | — |
| cyclophosphamide | 60 mg/kg × 1 | 15/15 | 19.93 ± 0.53 | 23.01 ± 1.04 | 1.38 ± 0.62 *** | 57.79 |

TABLE 1-continued

Anti-tumor effect of chlorogenic acid against mouse melanoma B16

| Groups | Dosage (mg/kg × time) | Animal No. Initial/End | Body weight (g) $\bar{x} \pm SD$ Initial | Body weight (g) $\bar{x} \pm SD$ End | Tumor weight (g) $\bar{x} \pm SD$ | Tumor inhibitory rate (%) |
|---|---|---|---|---|---|---|
| Chlorogenic acid | 5 mg/kg × 13 | 15/15 | 19.73 ± 0.53 | 22.55 ± 1.16 | 2.70 ± 0.76 | 17.23 |
| | 10 mg/kg × 13 | 15/15 | 19.93 ± 0.59 | 22.17 ± 1.76 | 1.83 ± 0.86 *** | 43.87 |
| | 20 mg/kg × 13 | 15/15 | 19.70 ± 0.68 | 21.78 ± 1.65 | 1.68 ± 0.69 *** | 48.66 |

Note:
*** P < 0.001, compared with the negative control group.

EXAMPLE 5 DRUG COMBINATION OF CHLOROGENIC ACID AND CYCLOPHOSPHAMIDE (1) Experimental Methods Mouse melanoma B16 model chooses male C57BL/6 mice, weighing 18-22 g. At the experiment, the tissue of tumor grown well was taken out, sheared, ground, filtered, and then diluted with sterile normal saline at a ratio of 1:3, to prepare suspension of tumor cells. 0.2 ml Tumor cell suspension was inoculated on the axillary back of each mouse. After inoculation, animals were divided into groups next day, weighed, and administration of drugs started. The dosage volume of cyclophosphamide injection was 0.2 ml/10 g mouse by intraperitoneal injection. Next day after inoculation, cyclophosphamide was injected once. For the chlorogenic acid-cyclophosphamide combination group, cyclophosphamide was firstly injected into left-side abdominal cavity, and then chlorogenic acid was injected into right-side abdominal cavity. The dosage volume of chlorogenic acid injection was 0.2 ml/10 g mouse by intraperitoneal injection, once a day, and the administration continued for 13 days.

Laboratory animals were divided into four groups, and they are respectively (1) negative control group, (2) 60 mg/kg cyclophosphamide group, (3) 60 mg/kg cyclophosphamide+10 mg/kg chlorogenic acid group, (4) 60 mg/kg cyclophosphamide+20 mg/kg chlorogenic acid group. Each group contains 15 animals. Next day after withdrawal of chlorogenic acid, animals were sacrificed and weighed, then tumors were peeled and weighed. Tumor control rate (%) was calculated based on tumor weight. Body weight and tumor weight were expressed as mean±standard deviation (x±SD). Each drug-administration group and the negative control group were compared.

(2) Experimental Results

Administration of chlorogenic acid to tumor-bearing mice by intraperitoneal injection shows obviously inhibitory action on growth of mouse melanoma B16, and presents certain dose-effect relationship. Tumor inhibitory rate of 20 mg/kg chlorogenic acid is close to that of cyclophosphamide. 20 mg/kg chlorogenic acid combined with cyclophosphamide can obviously improve anti-tumor effects of cyclophosphamide. At dosage used, chlorogenic acid did not have obvious effect on animal body weight, as shown in Table 2.

TABLE 2

Anti-tumor effect of chlorogenic acid-cyclophosphamide combination against mouse melanoma B16.

| Groups | Dosage (mg/kg × time) | Animal No. Initial/End | Body weight (g) $\bar{x} \pm SD$ Initial | Body weight (g) $\bar{x} \pm SD$ End | Tumor weight (g) $\bar{x} \pm SD$ | Tumor inhibitory rate (%) |
|---|---|---|---|---|---|---|
| Negative control group | | 15/15 | 19.22 ± 0.82 | 20.97 ± 1.06 | 3.77 ± 0.53 | — |
| cyclophosphamide | 60 mg/kg × 1 | 15/15 | 19.59 ± 0.81 | 22.58 ± 1.15 | 1.46 ± 0.54*** | 61.40 |
| Chlorogenic acid + cyclophosphamide | 10 mg/kg × 13 + 60 mg/kg × 1 | 15/15 | 19.45 ± 0.62 | 22.46 ± 1.23 | 1.08 ± 0.46*** | 71.26 |
| Chlorogenic acid + cyclophosphamide | 20 mg/kg × 13 + 60 mg/kg × 1 | 15/15 | 19.79 ± 0.88 | 22.70 ± 1.47 | 0.75 ± 0.26***### | 80.10 |

Note:
***P < 0.001, compared with the negative control group.
P < 0.001, compared with the cyclophosphamide group.

EXAMPLE 6 DRUG COMBINATION OF CHLOROGENIC ACID AND CISPLATIN (1) Experimental Methods Mouse melanoma B16 model chooses male C57BL/6 mice, weighing 18-22 g. At the experiment, the tissue of tumor grown well was taken out, sheared, ground, filtered, and then diluted with sterile normal saline at a ratio of 1:3, to prepare suspension of tumor cells. 0.2 ml Tumor cell suspension was inoculated on the axillary back of each mouse. Next day after inoculation, animals were divided into groups, weighed, and administration of drugs started. The dosage volume of adriamycin injection was 0.2 ml/10 g mouse by intraperitoneal injection. Single adriamycin and its combined drug were both administrated every other day, with total six successive administrations. The dosage volume of cisplatin injection was 0.2 ml/10 g mouse by intraperitoneal injection. Single cisplatin and its combined drug were both administrated every three days, with total three administrations. The dosage volume of chlorogenic acid injection was 0.2 ml/10 g mouse by intraperitoneal injection, once a day, and the administration continued for 11 days. For the drug combination group, chlorogenic acid was firstly injected into left-side abdominal cavity, and then adriamycin or cisplatin was injected into right-side abdominal cavity.

Laboratory animals were divided into seven groups, and they are respectively (1) negative control group, (2) 3 mg/kg adriamycin group, (3) 3 mg/kg cisplatin group, (4) 3 mg/kg adriamycin+10 mg/kg chlorogenic acid group, (5) 3 mg/kg adriamycin+20 mg/kg chlorogenic acid group, (6) 3 mg/kg cisplatin+10 mg/kg chlorogenic acid group, (7) 3 mg/kg cisplatin+20 mg/kg chlorogenic acid group. Each group contains 15 animals. Next day after withdrawal of chlorogenic acid, animals were sacrificed and weighed, then tumors were peeled and weighed. Tumor control rate (%) was calculated based on tumor weight. Body weight and tumor weight were expressed as mean±standard deviation ($\bar{x}\pm SD$). Test between each drug-administration group and the negative control group, between the chlorogenic acid+adriamycin group and the adriamycin group, and between the chlorogenic acid+cisplatin group and the cisplatin group were carried out.

$$\text{Tumor control rate (\%)} = \frac{\text{Tumor weight of negative control group} - \text{Tumor weight of drug-administration group}}{\text{Tumor weight of negative control group}} \times 100$$

(2) Experimental Results

Intraperitoneal injection of chlorogenic acid showed obviously inhibitory effect on growth of mouse melanoma B16, with obviously dose-effect relationship. 20 mg/kg chlorogenic acid can significantly potentialize the anti-tumor effect of adriamycin and cisplatin. From the mouse body weight, it can be seen that chlorogenic acid at used dosage did not have obvious effect, as shown in Table 3.

to prepare suspension of tumor cells. 0.2 ml Tumor cell suspension was inoculated on the axillary back of each mouse. Next day after inoculation, animals were divided into groups, weighed, and administration of drugs started. Normal saline was administrated to mice in the negative control group by peritoneal injection at 0.2 ml/10 g, once a day. The dosage volume of 5-flurouracil injection was 0.2 ml/10 g mouse by intraperitoneal injection. Next day after inoculation, 5-flurouracil single and its combined drug were injected once every three days. The dosage volume of chlorogenic acid injection was 0.2 ml/10 g mouse by intraperitoneal injection, once a day, and the administration continued for 14 days. For the chlorogenic acid-5-flurouracil combination group, chlorogenic acid was firstly injected into left-side abdominal cavity, and then 5-flurouracil was injected into right-side abdominal cavity.

Laboratory animals were divided into four groups, and they are respectively (1) negative control group, (2) 500 mg/kg 5-flurouracil group, (3) 500 mg/kg 5-flurouracil+10 mg/kg chlorogenic acid group, (4) 500 mg/kg 5-flurouracil+20 mg/kg chlorogenic acid group. Each group contains 12 animals. Next day after withdrawal of chlorogenic acid, animals were sacrificed and weighed, then tumors were peeled and weighed. Tumor control rate (%) was calculated based on tumor weight. Body weight and tumor weight were expressed as mean±standard deviation (x±SD). t-test between each drug-administration group and the negative control group, and t-test between each drug-combination group and the 5-flurouracil group were carried out.

$$\text{Tumor control rate (\%)} = \frac{\text{Tumor weight of negative control group} - \text{Tumor weight of drug-administration group}}{\text{Tumor weight of negative control group}} \times 100$$

TABLE 3

Anti-tumor effect of chlorogenic acid-adriamycin combination or chlorogenic acid-cisplatin combination against mouse melanoma B16

| Groups | Dosage (mg/kg × time) | Animal No. Initial/End | Body weight (g) $\bar{x} \pm SD$ Initial | Body weight (g) $\bar{x} \pm SD$ End | Body weight change rate (%) | Tumor weight (g) $\bar{x} \pm SD$ | Tumor inhibitory rate (%) |
|---|---|---|---|---|---|---|---|
| Negative control group | | 15/15 | 20.01 ± 0.91 | 27.66 ± 3.67 | — | 4.63 ± 0.99 | — |
| Adriamycin | 3 mg/kg × 6 | 15/15 | 19.65 ± 0.97 | 21.46 ± 3.53*** | 22.39 | 1.90 ± 0.56*** | 58.89 |
| Cisplatin | 3 mg/kg × 6 | 15/15 | 19.60 ± 0.60 | 21.14 ± 2.39*** | 23.57 | 1.58 ± 0.69*** | 65.97 |
| Chlorogenic acid + Adriamycin | 10 mg/kg × 11 + 3 mg/kg × 6 | 15/15 | 19.87 ± 0.97 | 21.99 ± 3.26*** | 20.48 | 1.70 ± 0.57*** | 63.25 |
| | 20 mg/kg × 11 + 3 mg/kg × 6 | 15/15 | 19.93 ± 0.64 | 20.49 ± 2.29*** | 25.91 | 1.34 ± 0.34***## | 71.01 |
| Chlorogenic acid + cyclophosphamide | 10 mg/kg × 11 + 3 mg/kg × 3 | 15/15 | 19.61 ± 0.56 | 19.73 ± 2.16*** | 28.65 | 1.49 ± 0.43*** | 67.86 |
| | 20 mg/kg × 11 + 3 mg/kg × 3 | 15/15 | 19.88 ± 0.72 | 21.51 ± 2.25*** | 22.22 | 1.13 ± 0.27***@ | 75.59 |

Note:
***P < 0.001, compared with the negative control group.
P < 0.01, compared with the adriamycin group.
@P < 0.05, compared with the cisplatin group.

EXAMPLE 7 DRUG COMBINATION OF CHLOROGENIC ACID AND 5-FLUOROURACIL (1) Experimental Methods Mouse melanoma B16 model chooses male BALB/c mice, weighing 18-22 g. At the experiment, the tissue of tumor grown well was taken out, sheared, ground, filtered, and then diluted with sterile normal saline at a ratio of 1:3, (2) Experimental Results Intraperitoneal injection of chlorogenic acid showed obviously inhibitory effect on growth of mouse melanoma B16, with obviously dose-effect relationship. 20 mg/kg chlorogenic acid can potentialize the anti-tumor effect of cyclophosphamide, without statistical difference. At used dosage, chlorogenic acid did not obviously change, as shown in Table 4.

TABLE 4

Tumor control rate of chlorogenic acid-5-flurouracil combination against mouse melanoma B16.

| Groups | Dosage (mg/kg × time) | Animal No. Initial/End | Body weight (g) $\bar{x} \pm SD$ Initial | Body weight (g) $\bar{x} \pm SD$ End | Tumor weight (g) $\bar{x} \pm SD$ | Tumor inhibitory rate (%) |
|---|---|---|---|---|---|---|
| Negative control group | | 12/12 | 19.27 ± 0.63 | 17.27 ± 1.42 | 2.24 ± 0.51 | — |
| 5-flurouracil | 500 mg/kg × 4 | 12/12 | 19.17 ± 0.72 | 18.30 ± 1.19 | 0.30 ± 0.18*** | 86.80 |
| Chlorogenic acid + 5-flurouracil | 10 mg/kg × 14 + 500 mg/kg × 4 | 12/12 | 18.88 ± 0.46 | 18.32 ± 0.82 | 0.34 ± 0.13*** | 84.80 |
| | 20 mg/kg × 14 + 500 mg/kg × 4 | 12/12 | 18.76 ± 0.63 | 17.83 ± 1.01 | 0.17 ± 0.11*** | 92.23 |

Note:
***P < 0.001, compared with the negative control group.

Macrophages participate the occurrence and progress of tumors, and different polarization types (M1, M2) of macrophages play different roles in tumorigenesis. M1-type macrophages kill tumor cells by various pathway; while M2-type macrophages take part in the process of tumor occurrence, growth, invasion and metastasis, and are usually shown to facilitate the process of the tumor growth, the tumor angiogenesis, and the metastasis of tumor cells, etc. Tumor local microenvironments encourage the differentiation of tumor-associated macrophages (TAMs) to M2-type macrophages. Investigation shows that TAMs behave as M1-type at initial stage of tumor, but behaves as M2-type at progression stage. Similarly, a large number of researches show that TAMs present in tumor tissues mostly behave as M2 phenotype, and are related to the treatment and prognosis of tumors.

Above experimental results show that chlorogenic acid treats melanoma and inhibits the metastasis of melanoma by the following pathway, i.e. promoting the polarization of monocytes to type M1 macrophages, retaining type M1 macrophages, and at the same time, suppressing transformation of type M1 macrophages to type M2 macrophages, facilitating transformation of type M2 macrophages to type M1 macrophages. Meanwhile, the tumor control rate of chlorogenic acid against mouse melanoma B16 models is close to that of chemotherapeutic drug cyclophosphamide, and possesses better tumor-inhibitory effect.

The present invention is not limited to above-mentioned examples. The present invention is expanded to any new feature or any new combination disclosed in the present specification, together with any new method or steps in the process or any new combination disclosed.

The invention claimed is:

1. A method for treating melanoma, comprising: administering an effective amount of chlorogenic acid and a chemotherapeutic drug to a subject in need thereof, wherein the chemotherapeutic drug is selected from the group consisting of cisplatin, 5-fluorouracil, adriamycin, and cyclophosphamide, wherein the effective amount of chlorogenic acid is 10-20 mg/kg.

2. The method of claim 1, wherein the effective amount of chlorogenic acid is in the form of a medicament comprising chlorogenic acid and one or more pharmaceutically acceptable excipients or auxiliary materials.

3. The method of claim 1, wherein the chemotherapeutic drug is adriamycin and a dosage of adriamycin is 3 mg/kg.

4. The method of claim 1, wherein the medicament is an injectable preparation or an oral preparation.

5. The method of claim 1, wherein the effective amount of chlorogenic acid regulates polarization of macrophages in melanoma tumor cells.

6. The method of claim 1, wherein the effective amount of chlorogenic acid and the chemotherapeutic drug are in a same preparation.

7. The method of claim 5, wherein chlorogenic acid promotes the formation of M1-type macrophages and inhibits the formation of M-2 type macrophages.

8. The method of claim 1, wherein the chemotherapeutic drug is cisplatin and a dosage of cisplatin is 3 mg/kg.

9. The method of claim 1, wherein the chemotherapeutic drug is cyclophosphamide and a dosage of cyclophosphamide is 60 mg/kg.

10. The method of claim 1, wherein the chemotherapeutic drug is 5-flurouracil and a dosage of 5-flurouracil is 500 mg/kg.

* * * * *